United States Patent
Antoniou

(10) Patent No.: US 7,815,925 B1
(45) Date of Patent: Oct. 19, 2010

(54) HAIR SPRAY FORMULA AND METHOD

(76) Inventor: John A. Antoniou, 2406 Timberlake, High Point, NC (US) 27265

( * ) Notice: Subject to any disclaimer, the term of this patent is extended or adjusted under 35 U.S.C. 154(b) by 1064 days.

(21) Appl. No.: 11/268,915

(22) Filed: Nov. 8, 2005

(51) Int. Cl.
- *A61K 8/02* (2006.01)
- *A61K 8/00* (2006.01)
- *A61K 8/19* (2006.01)
- *A61K 8/88* (2006.01)

(52) U.S. Cl. ............ 424/401; 424/70.1; 424/70.17
(58) Field of Classification Search .......... None
See application file for complete search history.

(56) References Cited

U.S. PATENT DOCUMENTS

| | | | | |
|---|---|---|---|---|
| 5,520,909 A | * | 5/1996 | Salce et al. | 424/70.51 |
| 5,599,524 A | * | 2/1997 | Morawsky et al. | 424/47 |
| 5,623,974 A | * | 4/1997 | Losenno et al. | 141/20 |
| 5,665,337 A | * | 9/1997 | Carballada et al. | 424/70.12 |
| 2004/0180066 A1 | * | 9/2004 | Lee et al. | 424/400 |

OTHER PUBLICATIONS

Liponic-EG-7 product data sheet, Lipo Chemicals, Inc., 2000- received from manufacturer on Mar. 3, 2008.*
Liponic-EG-7 product specification, Lipo Chemicals, Inc., Oct. 3, 1996- received from manufacturer on Mar. 3, 2008.*
Liponic EG-7 MSDS, Lipo Chemicals, Inc., Jan. 12, 2000—received from manufacturer on Mar. 3, 2008.*
Specification sheet and Chemical Product and Company Identification sheet for Gantrez ES-225, two pages.
Specification sheet for Olealkonium chloride, one page.
Specification sheet for Amphomer LV-71, one page.
Specification sheet and material safety data sheet for Aminomethyl propanol, trade name AMP-95, two pages.
Specification sheet for Honeysuckle # 11764, one page.
Specification sheet for Vitamin E Oil, one page.
Specification sheet and material safety data sheet for Benzophenone-4, two pages.
Certificate of Analysis for d 1-Panthenol, one page.
Data sheet for D-Panthenol 75W, two pages.
Specification sheet for Hexamethyl disiloxane, one page.
Specification sheet for Ethyl Ester of PVM/MA Copolymer, one page.
Company profile for International Specialty Products, Inc., two pages.

* cited by examiner

*Primary Examiner*—Johann R. Richter
*Assistant Examiner*—James H Alstrum Acevedo

(57) ABSTRACT

A hair spray formula for use on styled, wet or dry hair utilizing disiloxane for fast drying. The formula has a low VOC content to meet state regulations. The formula provides static control, UV protection and prevents the need for extensive re-spraying which can fade, load or dull the hair color.

2 Claims, No Drawings

HAIR SPRAY FORMULA AND METHOD

FIELD OF THE INVENTION

The invention herein pertains to hair cosmetic products and particularly pertains to a hair spray formula utilizing disiloxane for maintaining the hair in place.

DESCRIPTION OF THE PRIOR ART AND OBJECTIVES OF THE INVENTION

Solutions for spraying the hair of individuals has become increasingly popular in recent years to hold the hair in place after combing and styling. Such hair sprays generally include solvents with dissolved resins which adhere to hair strands that have been, for example combed, curled or brushed to obtain a particular aesthetic style. Such hair sprays prevent physical activities, wind and the like from disturbing the same. Due to the increase in the use of hair sprays, certain states have enacted environmental laws which limit the amount of volatile organic compounds (VOC) used in such sprays. Generally, 80% VOC is permitted however some states now limit the hair spray content to only 55% VOC. It is anticipated that even more stringent VOC standards will be enacted in the near future.

By reducing the amount of VOC present, conventional hair sprays require longer drying times which is a concern to stylists and others that must pause for the drying to occur during styling or combing the hair. Salon patrons also prefer a fast drying hair spray which will allow them to quickly and conveniently complete the styling process.

Conventional hair sprays are often relatively slow drying, attracting dust and debris, causing build-up and loading the hair. Some known hair sprays require re-application for proper "hold" and some hair sprays can cause hair color to fade or dull over time as no UV protection is provided.

Thus, in view of the problems and disadvantages of conventional hair sprays and methods of use the present invention was conceived and one of its objectives is to provide a relatively inexpensive liquid hair spray formula which drys quickly, repels dust, dirt and debris and has superior holding power.

It is another objective of the present invention to provide a hair spray formula which includes disiloxane and has a low VOC content.

It is still another objective of the present invention to provide a hair spray formula which includes benzophenone 4 which provides UV protection from the sun.

It is still a further objective of the present invention to provide a hair spray formula which is easy to manufacture.

It is yet a further objective of the present invention to provide a hair spray formula which gives the hair good "body" and sheen and is safe to the consumer and to the environment.

Various other objectives and advantages of the present invention will become apparent to those skilled in the art as a more detailed description is set forth below.

SUMMARY OF THE INVENTION

The aforesaid and other objectives are realized by providing a hair spray formula and method for treating the hair therewith. The hair spray formula will pass rigorous VOC standards and is fast drying. Disiloxane used in the hair spray formula can be varied from approximately 13% to 54% by weight while certain solvents, such as denatured ethyl alcohol, copolymers, fragrances, vitamins and other ingredients are included to form a clear, stable, fast drying formula. In the method of use, the hair spray formula is placed in a bottle with a conventional finger pump sprayer attached thereto. The hair is combed or brushed into the particular style desired and the hair spray formula is applied where it quickly dries to maintain the hair in place.

DETAILED DESCRIPTION OF THE PREFERRED EMBODIMENT AND OPERATION OF THE INVENTION

For a better understanding of the invention and its operation, the preferred hair spray formula is first set forth below:

| Formula - 55% VOC | | |
|---|---|---|
| | Chemical Ingredients | By Weight |
| a) | SD Alcohol 40-B | 55.00% |
| b) | Olealkonium Chloride | 1.70% |
| c) | Octylacrylamide/Acrylates/ butylaminoethyl methacrylate copolymer | 2.00% |
| d) | Aminomethyl Propanol | 0.38% |
| e) | Fragrance | 0.80% |
| f) | Vitamin E | 0.05% |
| g) | Glycereth 7 | 0.40% |
| h) | Benzophenone 4 | 0.04% |
| I) | Panthenol | 0.04% |
| j) | Disiloxane | 39.59% |
| | Total | 100.00% | a) Specially denatured ethyl alcohol formed by adding 1/16 avoirdupois ounce of denatonium benzoate and 1/8 gallon of tetrabutyl alcohol per 100 gallon of ethyl alcohol (90% ethyl alcohol; 10% water).
b) CAS Registry Number: 037139-99-4; Oleyl dimethyl benzyl ammonium chloride
c) Trade name Amphomer ® (28-4910) found on the website www.personalcarepolymers.com
d) 2-Amino-2-methyl-1-propanol (95%) and water (5%) as sold under the trade name AMP-95 by Angus Chemical Company, Northbrook, Illinois 60062
e) Honeysuckle #11746 - Product of Atlanta Fragrances Inc. Of Kennesaw, Georgia
f) Vitamin E Oil (97% min. USP 24) manufactured by Parchem Trading Ltd., White Plains, New York 10601
g) Sold by Lipo Chemicals Inc., Patterson, New Jersey 07504 under the name Liponic EG-7.
h) 2-benzoyl-5-methoxy-1-Phenol-4-sulfonic acid as sold under the trade name UVINUL * MS-40 of BASF Corporation, Parsippeny, New Jersey 07054
I) D1-Panthenol (99.3%) $C_9H_{19}O_4N$, Tri-K Industries, Northvale, New Jersey 07647
j) Hexamethyl disiloxane (99.0%) $[(CH_3)_3Si]_2O$ as sold by International Specialty Products, Wayne, New Jersey 07470

The chemical ingredients in the preferred method of manufacture are mixed at room temperature by measuring each ingredient, one after another into a standard mixing bowl and then stirring to create the preferred liquid hair spray formula. This formula can then be packaged into plastic containers (bottles) having standard manual finger pumps for delivery and sale.

The preferred method of use includes the following steps: after shampooing, combing and styling the hair, the user sprays the preferred formula on the hair in order to maintain a particular style. The formula will quickly dry to hold the hair in its styled configuration. The formula is stable and clear, having a VOC of 55%, meeting the most current, stringent state requirements. Other alternate formulas are listed below.

| Alternate Formula 2 - 41% VOC | | |
|---|---|---|
| | Chemical Ingredients | By Weight |
| a) | SD Alcohol 40-B | 41.00% |
| b) | Olealkonium Chloride | 1.70% |
| c) | Octylacrylamide/Acrylates/ butylaminoethyl methacrylate | 2.00% |

Alternate Formula 2 - 41% VOC

| | Chemical Ingredients | By Weight |
|---|---|---|
| | copolymer | |
| d) | Aminomethyl Propanol | 0.38% |
| e) | Fragrance | 0.80% |
| f) | Vitamin E | 0.05% |
| g) | Glycereth 7 | 0.40% |
| h) | Benzophenone 4 | 0.04% |
| I) | Panthenol | 0.04% |
| j) | Disiloxane | 53.59% |
| | Total | 100.00% |

Alternate Formula 3 - 45% VOC:

| | Chemical Ingredients | By Weight |
|---|---|---|
| a) | SD Alcohol 40-B | 45.00% |
| b) | Olealkonium Chloride | 1.70% |
| c) | Octylacrylamide/Acrylates/ butylaminoethyl methacrylate copolymer | 2.00% |
| d) | Aminomethyl Propanol | 0.38% |
| e) | Fragrance | 0.80% |
| f) | Vitamin E | 0.05% |
| g) | Glycereth 7 | 0.40% |
| h) | Benzophenone 4 | 0.04% |
| I) | Panthenol | 0.04% |
| j) | Disiloxane | 49.59% |
| | Total | 100.00% |

Alternate Formula 4 - 50% VOC:

| | Chemical Ingredients | By Weight |
|---|---|---|
| a) | SD Alcohol 40-B | 50.00% |
| b) | Olealkonium Chloride | 1.70% |
| c) | Octylacrylamide/Acrylates/ butylaminoethyl methacrylate copolymer | 2.00% |
| d) | Aminomethyl Propanol | 0.38% |
| e) | Fragrance | 0.80% |
| f) | Vitamin E | 0.05% |
| g) | Glycereth 7 | 0.40% |
| h) | Benzophenone 4 | 0.04% |
| I) | Panthenol | 0.04% |
| j) | Disiloxane | 44.59% |
| | Total | 100.00% |

Alternate Formula 5 - 60% VOC:

| | Chemical Ingredients | By Weight |
|---|---|---|
| a) | SD Alcohol 40-B | 60.00% |
| b) | Olealkonium Chloride | 1.70% |
| c) | Octylacrylamide/Acrylates/ butylaminoethyl methacrylate copolymer | 2.00% |
| d) | Aminomethyl Propanol | 0.38% |
| e) | Fragrance | 0.80% |
| f) | Vitamin E | 0.05% |
| g) | Glycereth 7 | 0.40% |
| h) | Benzophenone 4 | 0.04% |
| I) | Panthenol | 0.04% |
| j) | Disiloxane | 34.59% |
| | Total | 100.00% |

Alternate Formula 6 - 65% VOC:

| | Chemical Ingredients | By Weight |
|---|---|---|
| a) | SD Alcohol 40-B | 65.00% |
| b) | Olealkonium Chloride | 1.70% |
| c) | Octylacrylamide/Acrylates/ butylaminoethyl methacrylate copolymer | 2.00% |
| d) | Aminomethyl Propanol | 0.38% |
| e) | Fragrance | 0.80% |
| f) | Vitamin E | 0.05% |
| g) | Glycereth 7 | 0.40% |
| h) | Benzophenone 4 | 0.04% |
| I) | Panthenol | 0.04% |
| j) | Disiloxane | 29.59% |
| | Total | 100.00% |

Alternate Formula 7 - 70% VOC:

| | Chemical Ingredients | By Weight |
|---|---|---|
| a) | SD Alcohol 40-B | 70.00% |
| b) | Olealkonium Chloride | 1.70% |
| c) | Octylacrylamide/Acrylates/ butylaminoethyl methacrylate copolymer | 2.00% |
| d) | Aminomethyl Propanol | 0.38% |
| e) | Fragrance | 0.80% |
| f) | Vitamin E | 0.05% |
| g) | Glycereth 7 | 0.40% |
| h) | Benzophenone 4 | 0.04% |
| I) | Panthenol | 0.04% |
| j) | Disiloxane | 24.59% |
| | Total | 100.00% |

Alternate Formula 8 - 75% VOC:

| | Chemical Ingredients | By Weight |
|---|---|---|
| a) | SD Alcohol 40-B | 75.00% |
| b) | Olealkonium Chloride | 1.70% |
| c) | Octylacrylamide/Acrylates/ butylaminoethyl methacrylate copolymer | 2.00% |
| d) | Aminomethyl Propanol | 0.38% |
| e) | Fragrance | 0.80% |
| f) | Vitamin E | 0.05% |
| g) | Glycereth 7 | 0.40% |
| h) | Benzophenone 4 | 0.04% |
| I) | Panthenol | 0.04% |
| j) | Disiloxane | 19.59% |
| | Total | 100.00% |

| Alternate Formula 9 - 80% VOC: | | |
|---|---|---|
| | Chemical Ingredients | By Weight |
| a) | SD Alcohol 40-B | 80.00% |
| b) | Olealkonium Chloride | 1.70% |
| c) | Octylacrylamide/Acrylates/ butylaminoethyl methacrylate copolymer | 2.00% |
| d) | Aminomethyl Propanol | 0.38% |
| e) | Fragrance | 0.80% |
| f) | Vitamin E | 0.05% |
| g) | Glycereth 7 | 0.40% |
| h) | Benzophenone 4 | 0.04% |
| I) | Panthenol | 0.04% |
| j) | Disiloxane | 14.59% |
| | Total | 100.00% |

| Alternate Formula 10 - 70% VOC: | | |
|---|---|---|
| | Chemical Ingredients | By Weight |
| a) | SD Alcohol 40-B | 64.900% |
| b) | Olealkonium Chloride | 0.600% |
| c) | Ethyl Ester of PVM/MA Copolymer | 10.000% |
| d) | Aminomethyl Propanol | 0.150% |
| e) | Fragrance | 0.600% |
| f) | Vitamin E | 0.050% |
| g) | Benzophenone 4 | 0.040% |
| h) | Panthenol | 0.040% |
| i) | FD&C #1 & #4 (50/50 blend by weight) | 0.003% |
| j) | Disiloxane | 23.620% |
| | Total | 100.003% | c) 2-Butenedioic Acid (Z)-, Monoethyl Ester, Polymer with Methoxyethene as sold under the trade name GANTREZ ES-225 by ISP Technologies Inc., Wayne, New Jersey, 07470
i) Manufactured by Clark Colors, Inc. Of Brimfield, New Jersey

| Alternate Formula 11 - 75% VOC: | | |
|---|---|---|
| | Chemical Ingredients | By Weight |
| a) | SD Alcohol 40-B | 69.900% |
| b) | Olealkonium Chloride | 0.600% |
| c) | Ethyl Ester of PVM/MA Copolymer | 10.000% |
| d) | Aminomethyl Propanol | 0.150% |
| e) | Fragrance | 0.600% |
| f) | Vitamin E | 0.050% |
| g) | Benzophenone 4 | 0.040% |
| h) | Panthenol | 0.040% |
| I) | FD&C #1 & #4 (50/50 blend by weight) | 0.003% |
| j) | Disiloxane | 18.620% |
| | Total | 100.003% |

| Alternate Formula 12 - 80% VOC: | | |
|---|---|---|
| | Chemical Ingredients | By Weight |
| a) | SD Alcohol 40-B* | 74.900% |
| b) | Olealkonium Chloride | 0.600% |
| c) | Ethyl Ester of PVM/MA Copolymer | 10.000% |
| d) | Aminomethyl Propanol | 0.150% |
| e) | Fragrance | 0.600% |
| f) | Vitamin E | 0.050% |
| g) | Benzophenone 4 | 0.040% |
| h) | Panthenol | 0.040% |
| I) | FD&C #1 & #4 (50/50 blend by weight) | 0.003% |
| j) | Disiloxane | 13.620% |
| | Total | 100.003% |

All formulas shown are prepared and used in the same manner and preferred Formula 1 through alternate Formula 12 provide variations in the VOC percentages and in the drying times. The fastest drying time is provided by the formula having the lowest percentage of VOC. The drying times between Formula 1 and alternate Formula 12 are only a matter of seconds, depending on the degree of hair wetness, ambient room temperature and the like. All formulas contained herein provide sheen, UV protection, body and luster to the styled hair while also repelling dust, dirt and debris.

The illustrations and examples provided herein are for explanatory purposes and are not intended to limit the scope of the appended claims.

I claim:

1. A method of treating hair to hold it in place to complete a styling process consisting essentially of the steps of:
    a) providing a non-aqueous formula having a VOC range of 41-80% with disiloxane of approximately 13-54% by weight, octylacrylamide/acrylates/butylaminoethyl methacrylate copolymer of 2% by weight, olealkonium chloride of 1.70% by weight and SD alcohol of 41-80% by weight;
    b) spraying the hair with the formula; and
    c) allowing the sprayed hair to dry.

2. A method of treating hair consisting essentially of the steps of:
    a) providing a non-aqueous formula of approximately 13-54% of disiloxane by weight, octylacrylamide/acrylates/butylaminoethyl methacrylate copolymer of 2% by weight and SD alcohol of 41-80% by weight;
    b) placing the formula in a spray container;
    c) spraying the hair with the formula; and
    d) allowing the sprayed hair to dry.

\* \* \* \* \*